United States Patent
Clouatre et al.

(10) Patent No.: US 7,189,416 B2
(45) Date of Patent: *Mar. 13, 2007

(54) METHOD FOR STABLE AND CONTROLLED DELIVERY OF (−)-HYDROXYCITRIC ACID

(75) Inventors: Dallas L. Clouatre, Santa Monica, CA (US); James M. Dunn, Littleton, CO (US)

(73) Assignee: Glykon Technologies Group, LLC, Las Vegas, NV (US)

( * ) Notice: Subject to any disclaimer, the term of this patent is extended or adjusted under 35 U.S.C. 154(b) by 481 days.

This patent is subject to a terminal disclaimer.

(21) Appl. No.: 10/303,117

(22) Filed: Nov. 23, 2002

(65) Prior Publication Data

US 2004/0101555 A1    May 27, 2004

(51) Int. Cl.
*A61K 9/14* (2006.01)
*A61K 9/16* (2006.01)

(52) U.S. Cl. ...................... 424/494; 424/439
(58) Field of Classification Search ............... 514/574; 424/439, 451, 458, 464, 470, 497
See application file for complete search history.

(56) References Cited

U.S. PATENT DOCUMENTS

| | | | |
|---|---|---|---|
| 3,764,692 A | 10/1973 | Lowenstein | 424/279 |
| 4,609,675 A * | 9/1986 | Franz | 514/568 |
| 4,910,023 A * | 3/1990 | Botzolakis et al. | 424/470 |
| 5,225,197 A * | 7/1993 | Bolt et al. | 424/440 |
| 5,536,516 A | 7/1996 | Moffett et al. | 426/271 |
| 5,626,849 A | 5/1997 | Hastings et al. | 424/195.1 |
| 5,656,314 A | 8/1997 | Moffett et al. | 426/272 |
| 5,783,603 A | 7/1998 | Majeed et al. | 514/574 |
| 5,914,326 A | 6/1999 | McCarty et al. | 514/188 |
| 6,160,172 A | 12/2000 | Balasubramanyam et al. | 562/584 |
| 6,207,714 B1 | 3/2001 | Clouatre et al. | 514/574 |
| 6,221,901 B1 | 4/2001 | Shrivastava et al. | 514/458 |
| 6,395,296 B1 | 5/2002 | Balasubramanyam et al. | 424/439 |
| 6,447,807 B1 * | 9/2002 | Clouatre et al. | 424/494 |

OTHER PUBLICATIONS

Dallas L. Clouatre, et al. Method For Stable And Controlled Delivery Of (—)-Hydroxycitric Acid Nov. 23, 2002.
Clouatre, Dallas and Michael E. Rosenbaum. *The Diet and Health Benefits of HCA (Hydroxicitric Acid)*. (Keats Publshing, New Canaan, CT: 1994).
Drury, Heber. "*Garcinia cambogia*" in *The Useful Plants Of India*, 2nd Edition. (William H. Allen and Co., London: 1873) p. 220.
Heymsfield, Steven B, et al. *Garcinia cambogia* (hydroxycitric acid) as a potential antiobesity agent: a randomized control trial. JAMA. Nov. 11, 1998;280(18):1596-1600.; also, especially, Letters, JAMA 1999:282-235.
Ishihara K, Oyaizu S, Onuki K, Lim K, Fushiki T. Chronic (—)-hydroxycitrate administration spares carbohydrate utilization and promotes lipid oxidation during exercise in mice. J Nutr. Dec. 2000;130(12):2990-5.
Lewis, YS, Neelakantan S. (—)-Hydroxycitric acid—the principal acid in the fruits of *Garcinia cambogia* Desr. Phytochemistry 1965;4:619-625.
Lewis YS. Isolation and properties of hydroxycitric acid. In John M. Lowenstein, ed., vol. 13 in Methods in Enzymology, *Citric Acid Cycle* (New York: Academic Press, 1969) 613-619.
Loe Y, Bergeron N, et al. Time Course of Hydroxycitrate Clearance in Fasting and Fed Humans. FASEB Journal 15;4:632, Abs. 501.1, 2001.
Loe YC, Bergeron N, et al. Gas chromatography/mass spectrometry method to quantify blood hydroxycitrate concentration. Anal Biochem. May 1, 2001;292(1):148-54.
Publications & Information Directorate, Council of Scientific & Industrial Research. *The Useful Plants of India*. (New Delhi: Publications & Information Directorate, 1986) 229.
Rao RN, Sakariah KK. Lipid-lowering and antiobesity effect of (—)-hydroxycitric acid. Nutrition Research 1988;8(2):209-212.
Sugden MC, et al. Brown-adipose-tissue lipogenesis in starvation effects of insulin and (—)hydroxycitrate. Bioscience Reports 1982;2(5):289-297.
Sullivan C, Triscari J. Metabolic regulation as a control for lipid disorders. I. Influence of (—)-hydroxycitrate on experimentally induced obesity in the rodent. Am J Clin Nutr. May 1977;30(5):767-76.

* cited by examiner

*Primary Examiner*—Michael P. Woodward
*Assistant Examiner*—Marc C. Fitzgerald
(74) *Attorney, Agent, or Firm*—Foley & Lardner LLP; Michel Morency; James F. Ewing

(57) ABSTRACT

A method for making the potassium, sodium and other hygroscopic salts of (−)-hydroxycitric acid and mixtures thereof workable by initial treatment with a desiccating agent, such as fumed silicon dioxide. These may be further rendered non-hygroscopic and non-reactive in acidic media via subsequent encasement in hydrophobic and acidophobic polymers. The calcium and magnesium salts of (−)-hydroxycitric acid likewise can be rendered nonreactive in acidic media. The resulting products are suitable for tableting, encapsulation and use in other dry media for weight loss, appetite suppression, improvements in fat metabolism and postprandial lipemia and other pharmaceutical purposes. Further, the products of this invention can be made nonreactive as components of acidic liquid drink mixes and snack bars and can be used in the production of controlled release administration formats.

15 Claims, No Drawings

METHOD FOR STABLE AND CONTROLLED DELIVERY OF (−)-HYDROXYCITRIC ACID

BACKGROUND OF THE INVENTION

1. Field of the Invention

The invention is directed toward a novel process by which hygroscopic salts of (−)-hydroxycitric acid, either potassium (−)-hydroxycitrate, the preferred salt of (−)-hydroxycitric acid, or, alternatively, sodium or other hygroscopic salts of (−)-hydroxycitric acid, can be rendered suitable for tableting, encapsulation and use in dry media such as powders in meal replacements for weight loss and other pharmaceutical purposes. Furthermore, the product of this invention can be made nonreactive as a part of acidic drink mixes and acidic snack bars. This invention is further directed toward the production of controlled release versions of potassium, sodium or other salts of (−)-hydroxycitric acid which can be used to provide controlled release of the compound.

2. Description of Prior Art (−)-Hydroxycitric acid (abbreviated herein as HCA) a naturally-ocurring substance found chiefly in fruits of the species of *Garcinia,* and several synthetic derivatives of citric acid have been investigated extensively in regard to their ability to inhibit the production of fatty acids from carbohydrates, to suppress appetite, and to inhibit weight gain. (Sullivan, A. C., et al., American Journal of Clinical Nutrition 1977;30:767.) Numerous other benefits have been attributed to the use of HCA, including, but not limited to an increase in the metabolism of fat stores for energy and an increase in thermogenesis (the metabolism of energy sources to produce body heat in an otherwise wasteful cycle). One commonly offered explanation for the effects of HCA is that this compound inhibits the actions of cytoplasmic (cytosolic) ATP:citrate lyase. (D. Clouatre and M. E. Rosenbaum, *The Diet and Health Benefits of HCA (Hydroxicitric Acid),* 1994.) Weight loss benefits are ascribed to HCA, its salts and its lactone in U.S. Pat. No. 3,764,692 granted to John M. Lowenstein in 1973. Lowenstein described a variety of possible pharmaceutical salts of HCA based upon alkali metals, e.g., potassium and sodium, and alkaline earth metals, e.g., calcium and magnesium. The production of the potassium salt of HCA had been described in the scientific literature previous to Lowenstein's patent, but not in regard to its weight-loss properties. Research into HCA by scientists at the pharmaceutical firm of Hoffmann-La Roche revealed that the lactone form of HCA is far less effective than is the sodium salt of HCA for weight loss purposes, in part because the lactone form lacks the proper affinity for the receptor which is the target of the actions of HCA. However, the sodium salt has disadvantages for long-term administration, both because sodium possesses no positive metabolic effects with regard to obesity and because sodium has potential hypertensive actions as well as other drawbacks. Potassium, as a ligand for HCA, does not possess the disadvantages associated with sodium. Moreover, the absorption of the potassium salt of HCA is considered to be superior to that of the sodium salt owing to the greater rate of uptake of potassium in relation to sodium in most tissues.

Free (−)-hydroxycitric acid, calcium, magnesium and potassium salts of HCA and poorly characterized mixtures of two or more of these minerals, usually substantially contaminated with sodium, currently exist on the American market. Calcium/sodium salts have been sold widely since at least as early as 1994. Most of the HCA sold consists of calcium salts of varying purity. Aside from the potassium salt, all of these HCA forms suffer from problems in assimilation, a fact attested to by poor performance in controlled weight loss trials. For instance, the free acid form of (−)-hydroxycitric acid is extremely ionic and does not pass readily through the gut membranes. Free HCA has several further disadvantages. It undergoes rapid lacontonization, and, again, the lactone form has no appreciable physiological activity. Indeed, inclusion of any of the currently available mineral salts of HCA in a prepared beverage of acidic pH will lead to the development of the HCA lactone over time. The free acid form, moreover, has a tendency to be bound up and made unavailable to the body by soluble and insoluble fibers as well as by many other compounds. Likewise the potassium and sodium salts, if placed even only briefly in acidic or flavored beverages, typically will undergo color change or exhibit other signs of having undergone chemical interaction with the contents of the beverage. Finally, although there is some evidence to the effect that the free acid (not the lactone) is more active than is the calcium salt of HCA, there is also good evidence that the free acid and the lactone both are irritating to the GI-tract if consumed regularly in large amounts. Thus although a patent exists for the use of free (−)-hydroxycitric acid concentrate in food products (U.S. Pat. No. 5,536,516), the art taught therein offers no particular advantages for weight loss nor for other medicinal purposes.

The calcium and magnesium salts of HCA are poorly absorbed from the gastrointestinal tract because they are poorly soluble in aqueous media and because both of these minerals are saponified by bile acids and fats in the gut and/or are bound up by soluble and insoluble fibers or other substances in the diet or secreted during digestion. Some of these problems have been pointed out by medical researchers and admitted in print by at least one primary manufacturer of HCA products. (Heymsfield, Steven B, et al. JAMA 1998;280(18):1596–1600; Letters, JAMA 1999;282:235.) Moreover, there is no evidence that merely making calcium and magnesium salts of HCA more soluble, such as can be accomplished by adding small amounts of potassium and/or sodium and/or lactone, will solve the problem of assimilation. HCA is known to have three separate binding points, and simple chemical experimentation quickly shows that divalent ions, such as those of calcium and magnesium, cannot be readily separated by the application of other acids, such as human gastric acid, from the HCA once these minerals have been reacted with it. The action of stomach acid, however, may free one of the two valences of calcium or magnesium for attachment to fats, bile acids, gums, fibers, pectins, and so forth and so on, which is an undesirable outcome. For weight loss and other purposes, a minimally effective amount of HCA derived from its calcium salt requires the administration of between 12 and 15 grams of a 50% material, and this amount of calcium (−)-hydroxycitrate may lead to undesirably elevated levels of binding and excretion of other dietary minerals, such as zinc, aside from presenting difficulties in administration. Animal trials (not published) have further demonstrated that in order for the potassium salt to be maximally effective, the ligand must be fully bound to the HCA with only trivial amounts of contaminants, including other minerals or fibers or sugars. Hence the calcium and magnesium salts, either alone or in the form of various mixtures together or in combination with the potassium and sodium salts, are not preferred delivery forms for HCA.

Several recent international patent applications and at least one U.S. patent claim to have greatly improved the efficacy of HCA via its delivery as calcium, magnesium and admixtures of salts. For instance, WO 99/03464, filed 28

Jan. 1999, claims special benefits for "hydroxycitric acid compositions which comprise approximately 14 to 26% by weight of calcium, and approximately 24 to 40% by weight of potassium or approximately 14 to 24% by weight of sodium, or a mixture thereof, each calculated as a percentage of the total hydroxycitric acid content of the composition, together with dietary supplements and food products containing such compositions and methods for utilizing such compositions, dietary supplements and food products to reduce body weight in mammals are disclosed." However, research performed specifically with this compound showed that its assimilation is very poor even when taken on an empty stomach (Loe Y C, Bergeron N, Rodriguez N, Schwarz J M. Gas chromatography/mass spectrometry method to quantify blood hydroxycitrate concentration. Anal Biochem. 1, 2001 May 1;292(1):148–54) and that eating a meal shortly after taking it reduced its absorption by about 60%. (Loe Y, Bergeron N, Phan J, Wen M, Lee J, Schwarz J-M, Time Course of Hydroxycitrate Clearance in Fasting and Fed Humans, FASEB Journal, 15,4:632, Abs. 501.1, 2001.)

No proof is offered in WO 99/03464 that the proposed compound is superior to fully reacted calcium HCA with regard to assimilation. It also should be noted that inasmuch as *Garcina cambogia* is typically salted for drying in Asia with the subsequent extracts including large amounts of sodium and inasmuch as calcium salts of HCA have been sold in the U.S. since at least 1992, the realization that mixing a divalent ligand with a monovalent ligand in reacting HCA will yield a soluble, yet increasingly nonhygroscopic salt was known at least as far back as 1992. Several of the early Indian-supplied "potassium" salts were, in fact, mixtures of calcium, potassium and sodium (−)-hydroxycitrate. Of course, the amount of sodium allowed with this product will be in excess of that allowed on low sodium diets and additional sodium is ill-advised on any modern diet.

Another application by the same inventor as above, WO 00/15051, seeks to make calcium (−)-hydroxycitrate soluble by under-reacting the material, i.e., leaving a substantial amount of HCA lactone in the finished product. This procedure, however, does little to improve the uptake of HCA. The problems with the lactone are discussed above, and the lactone in large amounts is known to be irritating. (Ishihara K, Oyaizu S, Onuki K, Lim K, Fushiki T. Chronic (−)-hydroxycitrate administration spares carbohydrate utilization and promotes lipid oxidation during exercise in mice. J Nutr. 2000 December;130(12):2990–5.) Making calcium soluble, again, does nothing to prevent its saponification in the gut nor does this improve the general rate of assimilation of calcium. One must assume that the rate of uptake by the compound taught in this invention will be even worse than that tested by Loe Y, et al., as indicated with WO 99/03464 above. In any event, the process proposed in WO 00/15051 was anticipated by others and had already been published in English in 1997 (Sawada, H., et al. Effects of liquid garcinia extract and soluble garcinia powder on body weight change. Journal of Japan Oil and Chemicals/Nihon Yukagaku Kaishi 1997 December;46, 12:1467–1474) and many months earlier in Japanese.

A much more promising application is WO 02/014477, first applied for in 17 Aug. 2000, which relates to a composition comprising hydroxycitric acid (HCA) in combination with either one or both of garcinol and anthocyanin. However, one should note that the effects reported are not overwhelming. In eight weeks, the average weight loss, for instance, was 4 pounds versus 2.5 pounds for control. Using a higher dosage of potassium (−)-hydroxycitirate alone, Clouatre et al. in U.S. Pat. No. 6,447,807 reported an average weight loss over a three week period of 3 pounds per week. Still to be determined is whether the additive effect shown in WO 02/014477 extends beyond the mild response reported if higher dosages of either component are ingested. Moreover, in practice garcinol is a common contaminant of HCA products, hence this application is claiming a special virtue for a compound already typically present in the salts which have been used for clinical studies, i.e., extracts rather than synthesized pure (−)-hydroxycitric acid.

Finally, U.S. Pat. No. 6,221,901 discusses the preparation and employments of magnesium (−)-hydroxycitrate. Leaving aside the many difficulties with the claims of this patent, the dosages used to achieve the indicated results were massive. To achieve a hypotensive effect, for instance, the inventors fed their animals 500 mg/kg magnesium (−)-hydroxycitrate. Using the standard 5:1 multiplier for rat to human data, the dose of magnesium hydroxycitrate employed by Shrivastava et al. is equivalent to a human ingesting 100 mg/kg/day or 7 grams for the average-sized human subject. Of this amount, 45% would be elemental magnesium, hence we have the equivalent of a human ingesting approximately 3.15 grams of magnesium. The *Recommended Dietary Allowances,* 10th edition (National Research Council, 1989), indicates that most humans begin to suffer diarrhea at more than 350 mg/day. In other words, the test dose used by Shrivastava et al. is nearly 10 times the dose at which side effects would normally be expected to begin to appear. The diarrhea induced itself would lower blood pressure rapidly. Hence, with normal magnesium (−)-hydroxycitrate not only is there poor uptake, but also there is the danger of osmotic diarrhea. Clearly this compound is not the answer to issues of improving the delivery of (−)-hydroxycitirate.

The preferred salt of HCA for pharmaceutical use is potassium (−)-hydroxycitrate (abbreviated herein as KHCA). The mineral potassium is fully soluble, as is its HCA salt, and is known to possess cell membrane permeability which is 100 times greater than that possessed by sodium. However, the potassium salt of HCA, as is also true of the sodium salt, is extremely hygroscopic and thus not suitable under normal circumstances for the production of dry delivery forms. In drawing moisture to itself, KHCA will also tend to bind to available binding sites of compounds in its immediate environment, and this action often later will markedly impede the assimilation of KHCA from the gut. KHCA is also not suitable for liquid delivery forms inasmuch as KHCA in solution will slowly lactonize to an equilibrium which is dependent upon the pH. One recent patent (U.S. Pat. No. 5,783,603) does teach a technique for the production of KHCA, but this material is nonhygroscopic only under the conditions mentioned specifically in that patent, to wit, "milling, sifting, blending and packing said dried precipitate under nitrogen to obtain said potassium hydroxycitric acid [sic] composition." If left in the open air outside of a humidity-controlled environment, the KHCA produced according to that patented method will begin to absorb moisture within a few minutes. Except as a very minor ingredient, it cannot be used as a component of dry pharmaceutical or nutriceutical preparations.

Only one piece of prior art (the present inventors' own U.S. Pat. No. 6,447,807) teaches a method for making the hygroscopic salts of hydroxycitric acid workable, and that invention proposes a method distinct from that contained herein. No other prior art teaches the production of the relatively pure potassium salt of (−)-hydroxycitric acid in a form which is workable under those conditions necessary for tableting, encapsulation, the production of controlled release vehicles nor incorporation into dry powders, such as dry meal replacement mixes. No other prior art teaches a method of including potassium or other forms of HCA in liquid media without lactonization and no other prior art teaches a method by which KHCA may be delivered under controlled release. Likewise, no other prior art teaches the above with regard to sodium (−)-hydroxycitrate.

The lack of a method of producing a controlled release form of HCA, regardless of the salt used, has led to a problem in the delivery of the drug. Tests performed to establish the appetite-suppressing effects of HCA found that a single large oral dose or two divided oral doses totaling one fourth the size of the single dose resulted in a 10% or greater reduction in food consumption in experimental animals fed a high-sugar diet. This result continued over many weeks with the chronic ingestion of HCA. The requirement for at least two divided doses of HCA for efficacy is the only thoroughly established procedure to date.

Giving HCA as multiple doses, as is true of any drug, is inconvenient and is not supported by good patient compliance. Multiple doses given in the form of any of the current salts is also wasteful in that any material delivered to the body which is above the baseline or threshold necessary to produce benefits is simply an excess which is excreted. Controlled release of HCA would avoid both excess and waste, on the one one, and gaps in coverage, on the other hand. Controlled release makes it possible to simplify the dosage schedule to one daily administration. Moreover, it is to be expected that a smaller amount of HCA delivered by controlled release will provide benefits which are superior to those found with a larger amount of HCA supplied after a normal fashion in at least two dosages.

SUMMARY OF THE INVENTION

The present invention resolves problems with regard to the use of the potassium, sodium and other hygroscopic salts of (−)-hydroxycitric acid. A principle is provided by which the hygroscopic salts of (−)-hydroxycitric acid in their relatively pure and active forms, including especially the potassium salt, but also including the sodium salt, are rendered non-hygroscopic and stable (that is, not prone to lactonization, not readily subject to attachment to ligands which inhibit absorption or lead to excretion, and so forth as described previously) such that these HCA salts might be included in dry delivery formats, liquid delivery and in controlled-release vehicles. Moreover, the nonhygroscopic salts of (−)-hydroxycitric acid may also be protected against acid degradation, lactonization and undesirable ligand binding when exposed to acidic environments or other challenging conditions.

Objects and Advantages

The potassium salt of (−)-hydroxycitric acid is the most efficacious form of HCA to be used for human weight loss and for other pharmaceutical and/or neutraceutical purposes, followed secondarily for these purposes by the sodium salt. The potassium and the sodium salts of HCA present very similar difficulties in handling and manipulation. Potassium (−)-hydroxycitrate is extremely hygroscopic and tends to bind with water in the open air to form a non-palatable paste not suitable for use in tablets, capsules or powders. This material can be admixed with orange juice or water, but requires vacuum pouch sealing under a humidity-controlled atmosphere and is inconvenient for the patient to use. KHCA, moreover, is reactive with a large number of compounds (tannins, gums, fibers, pectins, and so forth) are thereby readily suffers large losses in pharmacological availability.

Using an acceptable, yet novel pharmaceutical art form for this product, the inventors have been successful in granulating the potassium salt form of (−)-hydroxycitric acid into a workable powder. This workable powder can be further manipulated according to the procedures taught in the present inventors' own U.S. Pat. No. 6,447,807 to produce a product which is acid resistant, retards water incursion into the material and can be formulated for controlled delivery. The same results can be extended to sodium and other salts of (−)-hydroxycitric acid and their mixtures. The present invention is a striking and elegant advance over the procedure taught in U.S. Pat. No. 6,447,807 in that it reduces or eliminates entirely the need to spray-dry the (−)-hydroxycitrate onto a separate carrier, such as maltodextrin, and reduces or removes steps requiring special spray or freeze drying. The present invention can substitute fluid bed drying for these latter processes. Because of these and other advantages, there are great savings in terms of time, equipment required and the addition of extra weight and volume to the finished product.

DESCRIPTION OF THE PREFERRED EMBODIMENTS

The raw material is the potassium salt of (−)-hydroxycitric acid which has been produced from the aqueous extract of *Garcinia cambogia,* other *Garcinia* species or by synthesis. In hydrated form it is a viscous deep brown. It has a earthy smell and contains approximately 6 parts by weight of solids per liter of fluid. The novel concept of this application is to show that a proper amount of desiccating agent can be admixed with the hydrated (−)-KHCA to make a granulate which can be then treated as a material for pharmaceutical formulation.

Methods of Preparation

The preferred agent for absorbing water out of the viscous KHCA is fumed silicon dioxide. This may be added to the starting material using a planetary mixer, such as a Hobart® mixer with a blade. In addition to silicon dioxide, a smaller portion of microcrystalline cellulose may be added to help strengthen the structure of the granulate, but this step is not essential to the proper working of this formulation.

The amount of silicon dioxide added to the wet viscous material can range from 2–40% by weight, depending upon the purity and quality of the KHCA used and the amount of water present in the starting material. KHCA contaminated with calcium, magnesium or certain other materials will require less silicon dioxide to achieve stability. With a sufficient content of divalent alkaline earth metals, the (−)-hydroxycitrate will become non-hygroscopic. However, these additives or contaminants will normally reduce the absorption of the HCA or otherwise reduce efficacy as already indicated. The amount of fumed silicon dioxide will be more preferably 15–30% by weight and the most preferred method is to add between 20–25% by weight. While the Hobart blade is stirring at a vigorous speed, slowly blend in the silicon dioxide until a very distinct granulate has formed and has the sound of sand stirring. When this has been accomplished, microcrystalline cellulose can be added in a range of 1–10% more preferably between 2–8% by weight and most preferably 3–5% by weight. When all the material is mixed, the granulate may still have moisture within its substance. This can be removed by air drying on a tray or blowing dry in a fluid bed drier at 40° C. until the granulate is dry and workable. It should then be placed through a screen such as a Fitzmill® or Quadromill® this will reduce the particles to a relatively even size. If moisture is still present the granulate should be blown dry in a fluid bed drier until measurements show a loss on drying of <2.5%. Once this is accomplished, the granulate should be coated with a polymer film which has enteric properties as taught in U.S. Pat. No. 6,447,807. Such polymers can be cellulose acetate phthalate, Eudragit L55®, and other known enteric products or mixtures thereof. The granulate is very hygroscopic so the polymer film should be sprayed on in a fluid bed chamber at 40° C. in a very slow manner so as to allow the moisture in the polymer to evaporate and not become intimately involved in the structure of the KHCA structure. After the granulate has been coated and dried, it should be blended with magnesium stearate and placed onto a rotary press and compressed into oblong tablets with a weight of 1,500 mg and a hardness of 10–15 kg fracture force.

The following are examples of encapsulation and tableting which may be performed with the KHCA powder produced from this novel procedure. With very little modification, the same examples can be applied to a powder produced from sodium (–)-hydroxycitrate by the novel procedure.

EXAMPLE 1

| Ingredient | Weight | Percent |
| --- | --- | --- |
| 1. KHCA Hydrated (35%) | 1.840 kg | 73.60% |
| 2. Silicon Dioxide | 0.632 kg | 25.80% |
| 3. Magnesium Stearate | 0.028 kg | 1.120% |
| Total | 2.500 kg | 100.00% |

The material noted above is placed in a Hobart® blender and thoroughly add mixed until a well formed granulate is formed. If the granulate is still moist, dry on air dying pans or in a fluid bed dryer. Following this, place the air drying trays or in a fluid bed drying chamber and dried until the LOD is <2.5%. Following drying reduce the particles by assign them through a high speed screening device such as a Fitzmill® or Quadromill®. After reduction in particle size place the granulate back into a fluid bed dryer and spray coat the granulate with an enteric polymer such as cellulose acetate phthalate or Eudragit L55® in an amount of 3–5% by weight of the finished granulate. This weight of polymer should be calculated into the final tablet weight. The material can also be used for capsules.

EXAMPLE 2

| Ingredient | Weight | Percent |
| --- | --- | --- |
| 1. KHCA Hydrated (35%) | 1.720 kg | 68.80% |
| 2. Silicon Dioxide | 0.632 kg | 25.28% |
| 3. Microcrystalline Cellulose | 0.120 kg | 4.800% |
| 4. Magnesium Stearate | 0.028 kg | 1.120% |
| Total | 2.500 kg | 100.00% |

As in Example I, ingredients 1+2 are added to the Hobart and blended before a distinct granulate forms, add microcrystalline cellulose and continue blending until a well formed distinct granulate has formed. After the granulate has formed continue drying on paper lined air drying trays or use the fluid bed dryer. When the granulate has a moisture content of less than <2.5% remove and reduce in size as noted previously. Place in fluid bed dryer and continue drying. While drying and the temperature is stable coat the particles with the appropriate weight of enteric polymer as mentioned in Example 1. When the material is coated and dry, remove from the dryer and place into a hopper of a rotary press and oblong tablets with a weight of 1,500 mg and a hardness of 10–15 kg fracture force. The material can also be used for capsules.

EXAMPLE 3

A less elegant manner of delivering the drug is in the form of a acidic shake or drink.

| Ingredient | Weight | Percent |
| --- | --- | --- |
| 1. KHCA (dry weight) | 1.80 kg (2.34 kg w/water) | 70.9% |
| 2. Silicon Dioxide | 0.54 kg | 21.3% |
| 3. Cellulose Acetate Phthalate | 0.16 kg | 6.3% |
| 4. Triethyl Citrate | 0.04 kg | ~1.6% (20–25% CAP) |
| 5. Talc (optional) | (optional) | 3–5% above total |
| 6. Acetone & Alcohol | Sufficient as carrier for CAP/TEC (1 × HCA mix) | Ratio of A:A may vary from approx. 1:1 to 3:1 |

The KHCA should contain approximately 30% water. This can be kneaded (add slowly, just as one adds water to flour in making bread) into dry $SiO_2$ weighing approximately 25–30% of the dry weight of the KHCA. The product must be mixed extremely well in a cool and dry environment to produce as small and uniform a particulate as possible. This particulate should be carefully dried at 50–60 C for several hours until completely dry and then ground or milled into a fine powder under a controlled atmosphere. (The addition of 10–15% CaHCA to the KHCA prior to processing with the $SiO_2$ should greatly improve handling and drying qualities.) The reason for the need for a fine powder is that agglomeration occurs during fluid bed coating and the particles may become so large that they will lodge on the bottom of the dryer and not be properly coated. Once the above process is complete, the powder will serve as the base for the coating with CAP/TEC. The coating should be completely dissolved in acetone and alcohol (A&A). (The coating may also be dissolved in an ammoniated water solution.) This mixture is then slowly sprayed on the KHCA/$SiO_2$ base to achieve a uniform coating. Talc may be added at the end of the cycle or to the resulting powder to prevent caking. The powder is dried as required, but the temperature should not exceed 95° C. This mixture is acid-resistant and will give a controlled delivery. The final product may be placed into capsules or stamped into tablets; properly handled, it can be used in drink mixes, meal replacements and other forms of delivery. To further entrap the KHCA, a cyclodextrin, such as hydroxy-propyl cyclodextrin or beta-cyclodextrin, may be added after the encasement with silicon dioxide.

CONCLUSIONS (−)-Hydroxycitrate has a multitude of metabolic functions. The literature teaches that the compound induces weight loss and decreases appetite in both animals and humans. The product in the preferred form of the potassium salt and in its secondarily preferred form as a sodium salt is highly soluble and extremely hygroscopic. It can be maintained as a powder only under controlled conditions. When manipulated by normal methods, it is unstable because of its sensitivity to acids and its extremely hygroscopic nature. Without special precautions, HCA in its free acid form and in its potassium and sodium salt forms will bind to numerous other compounds and thereby to become markedly less assimilable. Hence, neither of the preferred salts of (−)-hydroxycitric acid prior to the present teaching have been fully stable or workable as capsules, tablets, powders, in beverages or prepared snacks, or in controlled release vehicles. Similarly, full potency of the compound's preferred salts can be compromised by digestive actions. Prior art teaches a method of producing a KHCA product which is stable and non-hygroscopic only so long as it is packaged under a controlled atmosphere and thereafter protected from exposure to moisture.

The present invention teaches a method of using a proper amount of desiccating agent admixed with hydrated (−)-hydroxycitrate to make a granulate which can be then treated as a material for pharmaceutical formulation work. Use of a desiccating agent in this fashion is novel and unexpected. The preferred agent is fumed silicon dioxide. Once treated according to teachings of this invention, even the most hygroscopic salts of (−)-hydroxycitric acid become workable and amenable to subsequent treatment with plasticizers, enteric and acid resistant polymers, mucosal adhesives, cyclodextrin-related compounds, and other pharmaceutical agents. Employing the present invention, it is possible to produce from the salts of (−)-hydroxycitric acid a fine powder which is protected from acidic breakdown and from high humidity environments. Using the powder of this process, it is possible to encapsulate the material, tablet the product, to place the material into a dry drink or meal replacement powder, or to mix it into a liquid acidic drink formulation and acidic snack bars. The powder can further be manipulated to produce controlled release products.

We claim:

1. A method for stabilizing the salts of (−)-hydroxycitric acid with fumed silicon dioxide as the desiccating agent whereby said agent is admixed with hydrated (−)-hydroxycitrate to make a granulate which is then treated as a material for further pharmaceutical formulation by encasing the resulting powders consisting of the salts of (−)-hydroxycitric acid in acid resistant hydrophobic polymers to produce (−)-hydroxycitrate granulate resistant to environmental moisture, resistant to lactonization under acid environments and resistant to undesirable binding, said method comprising the steps of:
    (1) obtaining a salt of (−)-hydroxycitric acid or a combination of salts of (−)-hydroxycitric acid,
    (2) blending said salt or combination of said salts of (−)-hydroxycitric acid with a suitable fumed silicon dioxide, and
    (3) blending the resulting material with said acid resistant hydrophobic polymer wherein the polymer is selected from the group consisting of cellulose acetate phthalate, ethyl cellulose, zein, acrylic polymers, hydroxymethylpropylmethyl cellulose phthalate, polyvinyl acetate phthalate, cellulose acetate trimalleate, acrylic polymer plasticizers, polymers of poly lactic acid, polymers of glycolic acid, and mixtures thereof, wherein the encased powder product of steps (1), (2) and (3) is formulated into tablets, capsules, prepared dry drink mixes, prepared acidic liquid drinkable products and acidic edible bars.

2. The method in claim 1, wherein the desiccating agent is fumed silicon dioxide admixed at the rate of 20–25% by weight of the amount of (−)-hydroxycitrate on a dry weight basis.

3. The method of claim 1, wherein said salt or combination of said salts of (−)-hydroxycitric acid is further blended with cyclodextrin.

4. The method of claim 1, wherein said salt or combination of said salts of (−)-hydroxycitric acid is spray dried or freeze dried under a vacuum or processed using a fluid bed dryer prior to formulation into tablets, capsules, prepared dry drink mixes, prepared liquid drinkable products and edible bars.

5. The method of claim 1, wherein the resulting product is a controlled release formulation.

6. The method of claim 1, further comprising the steps of administering an effective amount of the resulting product to suppress appetite in a patient in need thereof.

7. The method of claim 1, further comprising the steps of administering an effective amount of the resulting product to inhibit cytoptasmic citrate lyase in a patient in need thereof.

8. The method of claim 1, further comprising the steps of administering an effective amount of the resulting product to increase fat metabolism in a patient in need thereof.

9. The method of claim 1, further comprising the steps of administering an effective amount of the resulting product to induce weight loss in a patient in need thereof.

10. The method of claim 1, wherein an effective amount of the resulting product is administered to reduce blood lipids and postprandial lipemia in a patient in need thereof.

11. The method of claim 1, wherein the resulting product is further admixed with pharmaceutical agents and excipients and formulated into tablets, capsules, prepared dry drink mixes, prepared acidic liquid drinkable products and acidic edible bars.

12. The method of claim 3, wherein the cyclodextrin is hydroxypropyl cyclodextrin.

13. The method of claim 5, wherein the controlled release formulation is administered once daily.

14. The method of claim 1, wherein the desiccating agent is fumed silicon dioxide admixed at the rate of 15–30% by weight of the amount of (−)-hydroxycitrate on a dry weight basis.

15. The method of claim 1, wherein the desiccating agent is fumed silicon dioxide admixed at the rate of 2–40% by weight of the amount of (−)-hydroxycitrate on a dry weight basis.

* * * * *

UNITED STATES PATENT AND TRADEMARK OFFICE
CERTIFICATE OF CORRECTION

| | | |
|---|---|---|
| PATENT NO. | : 7,189,416 B2 | Page 1 of 2 |
| APPLICATION NO. | : 10/303117 | |
| DATED | : March 13, 2007 | |
| INVENTOR(S) | : Dallas L. Clouatre, James M. Dunn and Daniel E. Clouatre | |

It is certified that error appears in the above-identified patent and that said Letters Patent is hereby corrected as shown below:

Title page, item [75] should read as follows
-- Inventors: Dallas L. Clouatre, Santa Monica, CA (US); Daniel E. Clouatre, Taipei (TW); James M. Dunn, Littleton, CO (US) --

At Column 10, lines 31 to 33, Claim 7 currently reads as follows:

"The method of claim 1, further comprising the steps of administering an effective amount of the resulting product to inhibit cytoptasmic citrate lyase in a patient in need thereof."

At Column 10, lines 31 to 33, please correct Claim 7 to read as follows:

-- The method of claim 1, further comprising the steps of administering an effective amount of the resulting product to inhibit cytoplasmic citrate lyase in a patient in need thereof. --

At Column 10, lines 43 to 47, Claim 11 currently reads as follows:

"The method of claim 1, wherein the resulting product is further admixed with pharmaceutical agents and excipients and formulated into tablets, capsules, prepared dry drink mixes, prepared acidic liquid drinkable products and acidic edible bars."

UNITED STATES PATENT AND TRADEMARK OFFICE
CERTIFICATE OF CORRECTION

PATENT NO. : 7,189,416 B2
APPLICATION NO. : 10/303117
DATED : March 13, 2007
INVENTOR(S) : Dallas L. Clouatre, James M. Dunn and Daniel E. Clouatre It is certified that error appears in the above-identified patent and that said Letters Patent is hereby corrected as shown below:

At Column 10, lines 43 to 47, please correct Claim 11 to read as follows:

-- The method of claim 1, wherein the resulting product is further admixed with pharmaceutical agents and excipients and formulated into tablets, capsules, prepared dry drink mixes, prepared acidic liquid drinkable products and acidic edible bars. --

Signed and Sealed this

Tenth Day of June, 2008

JON W. DUDAS
*Director of the United States Patent and Trademark Office*